United States Patent [19]
Sparks, deceased et al.

[11] 3,938,524
[45] Feb. 17, 1976

[54] COMPLIANT MANDREL AND MANDREL ASSEMBLY FOR GROWING GRAFT TUBES

[76] Inventors: Charles Howard Sparks, deceased, late of Portland, Oreg., by Margaret J. Sparks, executrix, 3725 SE. Martins St., Portland, Oreg. 97202

[22] Filed: Sept. 16, 1974

[21] Appl. No.: 506,214

Related U.S. Application Data

[60] Continuation-in-part of Ser. No. 368,811, June 11, 1973, Pat. No. 3,866,609, which is a continuation of Ser. No. 241,189, April 5, 1972, abandoned, Division of Ser. No. 101,031, Dec. 23, 1970, Pat. No. 3,710,777.

[52] U.S. Cl. ................. 128/303 R; 128/1 R; 3/1.4; 264/45.1; 3/1
[51] Int. Cl.² ...................... A61B 17/00; A61F 1/24
[58] Field of Search ...... 3/1, 1.4; 128/303 R, 334 R, 128/1 R, 335.5, DIG. 21

[56] References Cited
UNITED STATES PATENTS 3,284,562 11/1966 Stebleton ...................... 128/335.5 X
3,847,156 11/1974 Trumble ......................... 128/335.5

FOREIGN PATENTS OR APPLICATIONS 228,866 7/1969 U.S.S.R. ........................................ 3/1

*Primary Examiner*—Ronald L. Frinks
*Attorney, Agent, or Firm*—Lee R. Schermerhorn

[57] ABSTRACT

A mandrel of sponge rubber or gel has a tension element for withdrawing the mandrel from a graft tube grown from living tissue. In a first embodiment the tension element comprises a strip of cloth embedded in a sponge rubber mandrel. In a second embodiment the tension element comprises a rubber tube containing the sponge rubber and in a third embodiment the tension element comprises a rubber tube containing a gel. The mandrel assembly includes cloth reinforcing tubes surrounding the mandrel.

11 Claims, 4 Drawing Figures

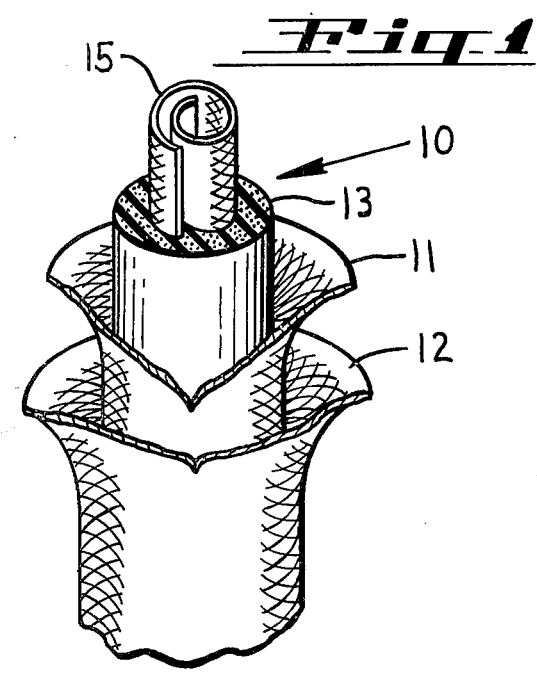
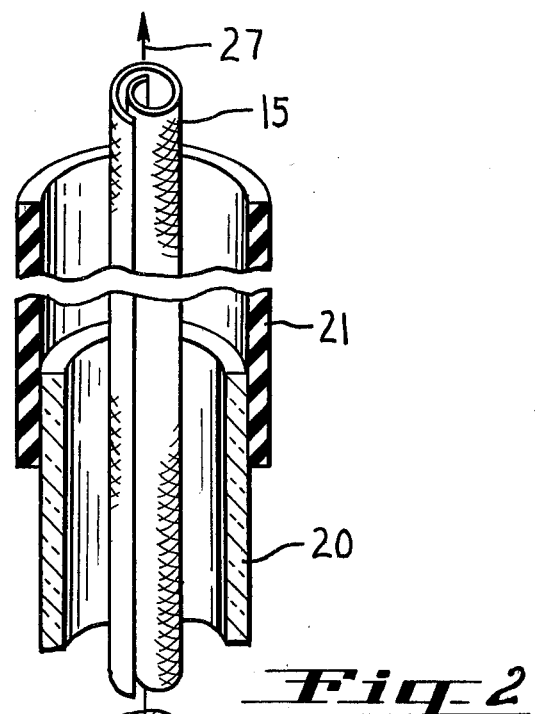
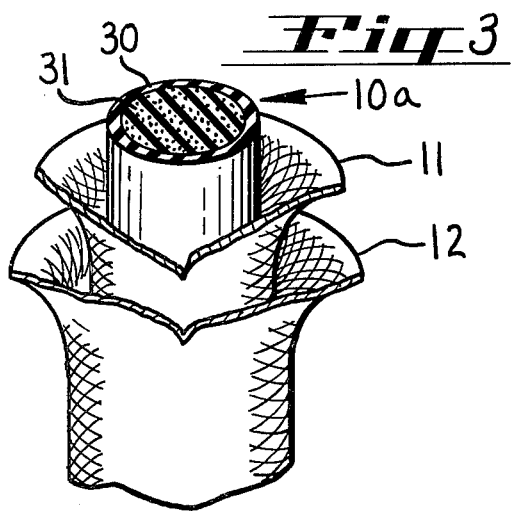
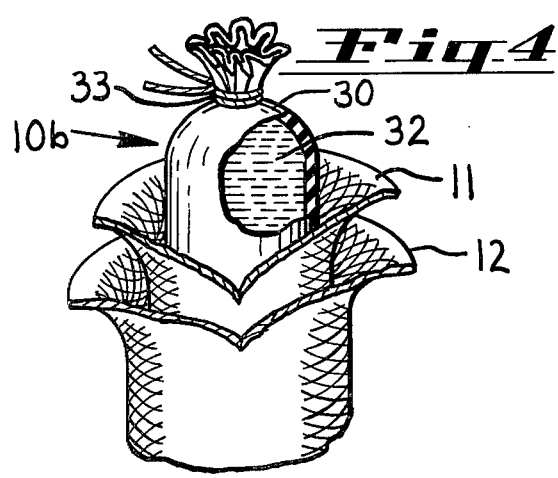
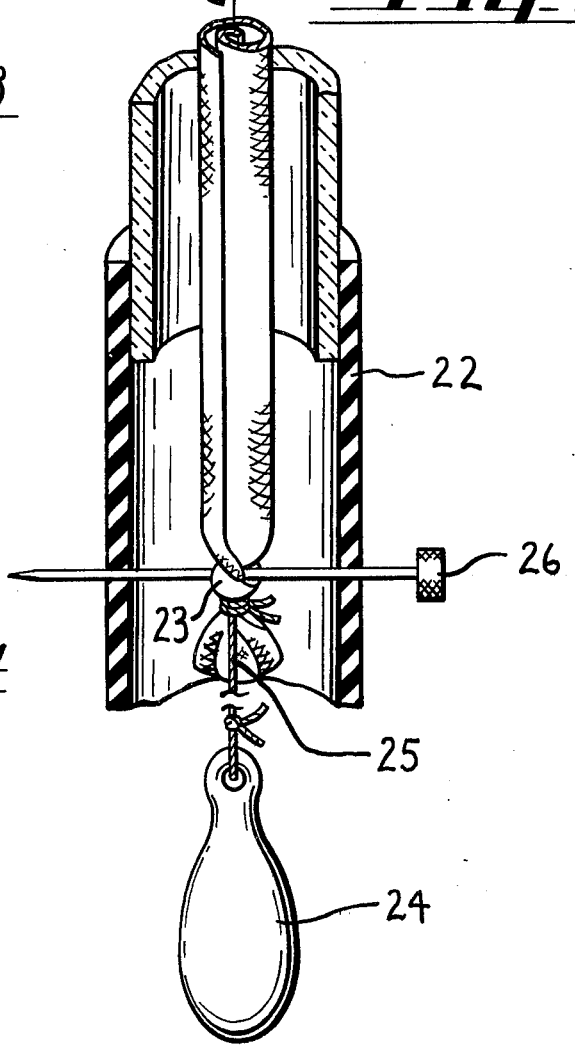

COMPLIANT MANDREL AND MANDREL ASSEMBLY FOR GROWING GRAFT TUBES

CROSS REFERENCES TO RELATED APPLICATIONS

This application is a continuation-in-part of my copending application Ser. No. 368,811 filed June 11, 1973, on Apparatus for Growing Graft Tubes in Place, now U.S. Pat. No. 3,866,609; which is a continuation of my application Ser. No. 241,189 filed Apr. 5, 1972 on Apparatus for Growing Graft Tubes in Place, now abandoned; which is a division of my application Ser. No. 101,031 filed Dec. 23, 1970 on Method and Apparatus for Growing Graft Tubes in Place, now U.S. Pat. No. 3,710,777.

BACKGROUND OF THE INVENTION

This invention relates to an improved mandrel and mandrel assembly for growing graft tubes of living tissue and to a method for making the mandrel.

In the related applications identified above, which are hereby incorporated by reference, a mandrel assembly having a pair of cloth tubes on a flexible silicone rubber mandrel is implanted in a living body to grow a graft tube in the place where it is to be used or to grow a transplantable graft tube which may be autogenous, homologous, or heterologous. Such graft tubes may be used as arteries, veins, esophagus, ureters, bile ducts, or trachea.

The mandrel assembly disclosed in said related applications has been used successfully for a considerable period of time by skilled surgeons. When the mandrel assembly is implanted in a living body, connective tissue from the body grows through the double layers of the cloth to thoroughly encapsulate the cloth and fill both an inner space between the inner cloth layer and the mandrel and an intermediate concentric annular space between the two layers of cloth.

The inner layer of cloth serves primarily as a spacer element to hold the outer layer of cloth away from the mandrel, and the filling of the inner and intermediate spaces just mentioned assists in this purpose. Thus, the outer layer of cloth provides a primary reinforcement to strengthen the graft tube adjacent its outer surface where reinforcement is most effective. The inner cloth tube also provides additional or secondary reinforcement, the two layers of cloth thereby greatly strengthening the wall of natural body tissue.

When the graft is grown in situ, or the place where it is to be used, the graft tube is completely vascularized and is a living part of the body when the ingrowth of tissue is complete and the mandrel withdrawn, leaving a lumen in the tube. The ends of the graft tube are then anastomosed to the tube or tubes of the body which the graft tube is to serve.

When the graft tube is to be transplanted to another location in the same body, or to a different body, it is similarly completely vascularized during its period of growth but upon transplant it must establish a new blood supply system and when the new blood supply is established, the graft becomes a living part of the body in which it is implanted.

The objects of the present invention are to provide an improved mandrel and mandrel assembly for growing a graft tube, to provide a mandrel and mandrel assembly which do not require as much skill on the the part of the surgeon, to provide a mandrel and mandrel assembly which will more consistently grow graft tubes of uniform quality, to provide a more compliant mandrel, and to provide a method for making a compliant mandrel.

SUMMARY OF THE INVENTION

The task of the surgeon is made less difficult and exacting by using a more compliant mandrel to form the lumen. A more compliant mandrel also provides greater flexibility for growing graft tubes for the different purposes mentioned above. In one form of construction a compliant mandrel is made of foam or sponge rubber which has a relatively soft and yielding texture. Since foam rubber is deficient in tension, a separate tension element may be incorporated in the mandrel in order to withdraw the mandrel from the graft tube when the growth of the graft tube is completed. This tension element may be a strip of cloth molded into the mandrel. A method for making such a mandrel is described in detail.

Other embodiments of compliant mandrel comprise a thin tube of silicone rubber filled with sponge rubber or silicone jelly. In such cases the silicone rubber tube provides the tension element for withdrawing the mandrel from the completed graft tube.

The invention will be better understood and additional objects and advantages will become apparent from the following description of the preferred embodiments illustrated on the accompanying drawing. Various changes may be made in the details of construction and in the methods of fabrication and certain features may be used without others. All such modifications within the scope of the appended claims are included in the invention.

BRIEF DESCRIPTION OF THE DRAWING

FIG. 1 is a fragmentary perspective view of a mandrel assembly with parts broken away to show a mandrel embodying the invention;

FIG. 2 is a longitudinal sectional view with parts broken away illustrating the method and apparatus employed in making the mandrel in FIG. 1;

FIG. 3 is a view similar to FIG. 1 showing a modification of the mandrel; and

FIG. 4 is a view similar to FIGS. 1 and 3 showing a further modification.

DESCRIPTION OF THE PREFERRED EMBODIMENTS

FIG. 1 shows a mandrel assembly having a compliant cylindrical mandrel 10 inserted in an inner cloth tube 11 and an outer cloth tube 12. The reenforcing tubes 11 and 12 are preferably made of a knitted Dacron material which has been impregnated with a suitable stiffening agent such as silicone rubber vulcanized in situ as described in the related applications identified above. Tube 11 has an inside diameter slightly exceeding the outside diameter of mandrel 10, and tube 12 has an inside diameter slightly exceeding the outside diameter of tube 11.

When this mandrel assembly is implanted in a living body or placed in a suitable culture, living tissue grows through the porous tubes 12 and 11 filling the annular space between these tubes and also filling the annular space between tube 11 and mandrel 10 whereby the tubes 11 and 12 form reenforcing members for a graft tube of living tissue.

Mandrel 10 has a smooth surface which casts a smooth lumen in the graft tube. The smooth surface on mandrel 10 is also essential for removal of the mandrel after the ingrowth of tissue through reenforcing cloth tubes 11 and 12 has been completed. After being grown in a living body, the resulting graft tube may be used in the place where it is grown, it may be transplanted to a different location in the same body, or it may be transplanted to a different living body. When grown in a culture, the mandrel 10 is removed and the graft tube implanted where needed in a living body.

The present invention is concerned essentially with the mandrel per se. Mandrel 10 comprises an elongated cylindrical body of silicone sponge rubber 13 having a smooth outer surface. Since the sponge rubber lacks sufficient strength, an internal tension element 15 is provided for pulling the mandrel out of the graft tube after the ingrowth of tissue has been completed. In FIG. 1 the tension element 15 comprises a strip of cloth which is preferably a knitted Dacron tube similar to or identical to the tube 11 or the tube 12. Cloth element 15, however, is not impregnated with silicone rubber vulcanized in situ as are tubes 11 and 12.

FIG. 2 illustrates the method of making mandrel 10. A casting, molding of forming tube 20 is suspended in a vertical position. Tube 20 has an inside diameter equal to the desired outside diameter of the sponge rubber body 13. The inside surface of tube 20 must be smooth so as to cast a smooth surface on the sponge rubber body. Tube 20 may be made of Teflon or vinyl plastic or it may be a glass tube coated on the inside with a suitable release agent. The upper end of tube 20 is fitted with a short length of rubber or transparent plastic tubing 21 and the lower end is similarly fitted with a piece of tubing 22.

Knitted Dacron tube 15 is carefully slit longitudinally and one end is tied in a knot 23. A weight 24 is attached to this end with a thread 25. Slit cloth tube 15 is lowered through the casting tube 20 until the knot 23 is disposed in tube 22 below the lower end of tube 20. Then a pin 26 is inserted through tube 22 and knot 23 and adjusted to as to position the knot on the center line of tube 20. Weight 24 is cut off and removed.

When the upper end of cloth 15 which is emergent from the upper end of tube 21 is drawn upward with light tension as indicated by arrow 27, the slit tube is stretched slightly in a longitudinal direction causing it to curl or roll as shown, reducing its diameter. The upper end of cloth 15 is thus held carefully under a light tension in a position to place the cloth as close as possible to the center line of casting tube 20. The reduction in diameter by the curled configuration of cloth tube 15 resulting from the upward tension at 27 holds the cloth spaced away from the inside wall of tube 20.

A suitable sponge rubber may be made from Silastic No. 386 foam elastomer with catalyst No. 708 (stannous octoate) supplied by Dow Corning Company. These materials are mixed and injected under low pressure into the lower end of tube 22 producing a foaming mixture which rises up through casting tube 20.

At the same time, the mixture fills and completely impregnates the curled cloth strip 15, causing this tension member to be integrally interlocked with the entire length of the column of sponge rubber which results from the setting of the elastomer. The operation must be carried out so that the gas bubbles generated in the elastomer are small in size and completely enclosed by elastomer. The upward injection in the manner described prevents the inclusion of air bubbles in the elastomer. During injection cloth strip 15 is maintained in the center of casting tube 20.

When the elastomer has set, pin 26 is withdrawn, tubes 21 and 22 are removed, and the resulting mandrel 10 is pulled out of tube 20. Cloth strip 15 has a degree of longitudinal elasticity characteristic of knitted fabric which is desirable for the present purpose. When the mandrel 10 is to be withdrawn from a graft tube having living tissue encapsulating the reenforcing tubes 11 and 12 and filling the space between tube 11 and the mandrel, a pull exerted on one end of strip 15 stretches both strip 15 and sponge rubber body 13 to some extent, elongating the mandrel and slightly contracting its diameter and thereby releasing the mandrel from the grip of the surrounding tissue.

Also characteristic of knitted fabric, a relatively small amount of elongation causes the fabric to reach its limit of stretch so that the sponge rubber is not stretched to the point of rupture. The knitted configuration of loose loops of thread behaves as a loose chain. When the links are pulled tight on each other there is no further elongation of the fabric and the full tensile strength of the threads is developed for pulling the mandrel out of the graft tube without over-stressing the sponge rubber in tension.

In the modification in FIG. 3, the mandrel 10a has an external tension element 30 comprising a thin walled silicone rubber tube. This tube is filled with sponge rubber 31 which may be the same silicone sponge rubber indicated at 13 in FIg. 1. Tube 30 has a smooth external surface to cast a smooth lumen in the living tissue of the graft tube.

In the modification in FIG. 4, the mandrel 10b has an external tension element in the form of a silicone rubber tube as in FIG. 3. In this case the tube 30 is filled with a silicone rubber gel 32. The ends of tube 30 are tied with ligatures 33 to retain the gel.

In the mandrel assembly in FIG. 3 the sponge rubber core 31 is significantly weak in tension. In the mandrel assembly in FIG. 4 the gel 32 is substantially without any strength in tension. In each case the tube 30 provides a tension element for withdrawing the mandrel from the graft tube. When a pulling force is exerted on one end of tube 30, the mandrel elongates slightly, producing a contraction of its diameter which facilitates withdrawal.

In the related applications referred to, the mandrel is a solid silicone rubber rod having only sufficient flexibility to move with movements of the body in which it is implanted as, for example, the movements of the knee and hip joints. Experience indicates, however, that far greater flexibility is desirable both to simplify the surgery and to accommodate implantation in other regions of the body in certain cases.

It is also found that in some cases a solid silicone rubber rod has too much longitudinal rigidity, causing movements of the ends of the rod when the rod is flexed. This impairs the quality and uniformity of the graft tube and complicates the surgery in order to insure good results. It is desired to have no longitudinal movement of the mandrel under bending.

The present mandrels 10, 10a and 10b avoid these difficulties. These mandrels are compliant to the body and substantially limp. This is true of the tension element in each embodiment as well as the body material of sponge rubber or gel. Bending does not produce longitudinal movement. Even when the location in the body causes the mandrel to be partially flattened, the quality of the graft tube is not impaired. Flattening does not diminish the circumferential dimension and the graft tube is free to resume circular shape with the full intended cross section area of the lumen available in use.

In the case of mandrel assemblies for growing tracheal and esophageal graft tubes, a tension element may not be necessary for pulling a sponge rubber mandrel out of the graft tube after the growth of the graft tube is completed. These graft tubes have much larger diameters and shorter lengths than graft tubes for blood vessels and the sponge rubber mandrels may be readily pushed out of the completed graft tubes.

Having now described my invention and in what manner the same may be used, what I claim as new and desire to protect by Letters Patent is:

1. A mandrel assembly for growing a graft tube with living tissue, comprising an elongated compliant mass of material which may not have sufficient tensile strength for withdrawing the mandrel from said mandrel assembly after said graft tube has been grown, and a compliant tension element extending throughout the length of the mandrel and forming an integral part thereof for pulling the mandrel out of said mandrel assembly after said graft tube has been grown, an outer fabric tube on said mandrel, and an inner layer of porous material holding said fabric tube spaced away from said mandrel.

2. A mandrel assembly as defined in claim 1, said tension element being disposed within said compliant mass of material.

3. A mandrel assembly as defined in claim 2, said compliant mass of material comprising sponge rubber.

4. A mandrel assembly as defined in claim 2, said tension element comprising a strip of cloth.

5. A mandrel assembly as defined in claim 1, said tension element comprising a rubber tube containing said compliant mass of material.

6. A mandrel assembly as defined in claim 5, said compliant mass of material comprising sponge rubber.

7. The invention of claim 1, said inner layer of porous material comprising an inner fabric tube within said outer fabric tube.

8. A mandrel for use in a mandrel assembly for growing a graft tube with living tissue, comprising an elongated compliant mass of material which may not have sufficient tensile strength for withdrawing the mandrel from said mandrel assembly after said graft tube has been grown, and a compliant tension element extending throughout the length of the mandrel and forming an integral part thereof for pulling the mandrel out of said mandrel assembly after said graft tube has been grown, said tension element comprising a strip of cloth disposed within said compliant mass of material, said strip of cloth comprising a longitudinally slit tube of said cloth.

9. A mandrel as defined in claim 8, said slit cloth tube comprising a knitted material.

10. A mandrel for use in a mandrel assembly for growing a graft tube with living tissue, comprising an elongated compliant mass of material which may not have sufficient tensile strength for withdrawing the mandrel from said mandrel assembly after said graft tube has been grown, and a compliant tension element extending throughout the length of the mandrel and forming an integral part thereof for pulling the mandrel out of said mandrel assembly after said graft tube has been grown, said tension element comprising a rubber tube containing said compliant mass of material, said compliant mass of material comprising a gel.

11. A mandrel assembly for growing a graft tube with living tissue, comprising a sponge rubber mandrel, an inner cloth tube on said mandrel impregnated with silicone rubber which is vulcanized in the cloth leaving the cloth porous, and an outer cloth tube surrounding said inner tube and mandrel, said outer tube being impregnated with silicone rubber which is vulcanized in the cloth leaving the cloth porous.

* * * * *